(12) United States Patent
Henkens et al.

(10) Patent No.: US 11,980,646 B2
(45) Date of Patent: May 14, 2024

(54) AEROSOL SPRAY CONTAINING VIABLE BACTERIAL SPECIES

(71) Applicants: YUN NV, Aartselaar (BE); Universiteit Antwerpen, Antwerp (BE)

(72) Inventors: Tim Henkens, Aartselaar (BE); Filip Kiekens, Wilrijk (BE); Sarah Lebeer, Antwerp (BE); Ingmar Claes, Antwerp (BE)

(73) Assignees: YUN NV, Aartselaar (BE); UNIVERSITEIT ANTWERPEN, Antwerp (BE)

( * ) Notice: Subject to any disclaimer, the term of this patent is extended or adjusted under 35 U.S.C. 154(b) by 1034 days.

(21) Appl. No.: 16/344,630

(22) PCT Filed: Oct. 27, 2017

(86) PCT No.: PCT/EP2017/077547
§ 371 (c)(1),
(2) Date: Apr. 24, 2019

(87) PCT Pub. No.: WO2018/078067
PCT Pub. Date: May 3, 2018

(65) Prior Publication Data
US 2020/0179464 A1 Jun. 11, 2020

(30) Foreign Application Priority Data
Oct. 28, 2016 (BE) .................................. 2016/5812

(51) Int. Cl.
*A61K 9/00* (2006.01)
*A61K 9/12* (2006.01)
*A61K 35/744* (2015.01)
*A61K 47/24* (2006.01)

(52) U.S. Cl.
CPC .......... *A61K 35/744* (2013.01); *A61K 9/0014* (2013.01); *A61K 9/12* (2013.01); *A61K 9/124* (2013.01); *A61K 47/24* (2013.01)

(58) Field of Classification Search
CPC ...... A61K 35/744; A61K 9/0014; A61K 9/12; A61K 9/124; A61K 47/24
See application file for complete search history.

(56) References Cited

U.S. PATENT DOCUMENTS

| 3,964,649 A | * | 6/1976 | Alexander | ........... B65D 83/663 |
| | | | | 222/399 |
| 2003/0003107 A1 | * | 1/2003 | Farmer | .................. A61K 8/925 |
| | | | | 424/184.1 |
| 2005/0196480 A1 | | 9/2005 | Sullivan | |
| 2008/0107699 A1 | * | 5/2008 | Spigelman | ............. A01N 63/34 |
| | | | | 424/404 |
| 2012/0328586 A1 | | 12/2012 | Lang | |
| 2014/0147425 A1 | * | 5/2014 | Henn | ...................... A61K 35/74 |
| | | | | 424/93.4 |
| 2016/0008412 A1 | | 1/2016 | Putaala | |

FOREIGN PATENT DOCUMENTS

| EP | 1661982 A1 | 5/2006 | |
| WO | WO-2005120235 A2 | * 12/2005 | ............. A01N 25/06 |

OTHER PUBLICATIONS

Anonymous. ISOBUTANE, Pubchem, downloaded from http://www.pubchem.ncbi.nlm.nih.gov/compound/isobutane on Mar. 30, 2022. (Year: 2022).*
Anonymous. Silica, Amorphous (Fume), New Jersey Department of Health and Senior Services, Hazardous Substance Fact Sheet, downloaded from http://www.nk.gov/health/eoh/rtkweb/documents/fs/1655.pdf on Mar. 29, 2022. (Year: 2003).*
Perrota, K. Spray and Go Moisturizer Review; Allure, pp. 1-6, downloaded from: https://www.allure.com/review/vaseline-spray-go-moisturizer on Jul. 20, 2022. (Year: 2013).*
Anonymous. Fumed Silica Powder; Reade, pp. 1-5, downloaded from: https://www.reade.com/products/fumed-silica-powder-sio2 on Jul. 20, 2022. (Year: 2022).*
Anonymous. 1,1,1,2-Tetrafluorethane, Pubchem, downloaded https://pubchem.ncbi.nlm.nih.gov/compound/13129 on Dec. 15, 2022. (Year: 2022).*
Winarno et al. Effect of Edta on the Germination of and Outgrowth From Spores of Clostridium Botulinum 62-A; Journal of Food Science, vol. 36, pp. 781-785. (Year: 1971).*
International Search Report dated Jan. 16, 2018, in reference to co-pending European Patent Application No. PCT/EP2017/077547 filed Oct. 27, 2017.
Anonymous: "Amazon.com: My Amazing Blow Dry Secret Leave-In Spray Conditioner, Floral Fusion, 12.0 Ounce: Beauty", Feb. 27, 2016 (Feb. 27, 2016). XP55364048.
Database GNPD [Online] MINTEL; Nov. 1, 2014 (Nov. 1, 2014), "Deo Man", XP002769193, Database accession No. 2799803.
Database GNPD [Online] MINTEL; Dec. 1, 2008 (Dec. 1, 2008), "Moisture Milk", XP002776772.
Database GNPD [Online] MINTEL; Dec. 1, 2010 (Dec. 1, 2010), "Milk fresh", XP002776773.
J Schrezenmeir: "Probiotics, prebiotics, and synbiotics-approaching a definition", Am J Clin Nutr 2001;73(suppl), Dec. 31, 2001 (Dec. 31, 2001), pp. 361S-364S, XP55364468.

(Continued)

*Primary Examiner* — Jeanette M Lieb
*Assistant Examiner* — Paul C Martin
(74) *Attorney, Agent, or Firm* — Dinsmore & Shohl LLP (57) ABSTRACT

Aerosol sprays are provided that include one or more bacterial species and at least one siloxane suitable for applying said one or more bacterial species to a surface or into the environment. Such sprays may also include a propellant under pressure. Such aerosol sprays may be used for restoring or maintaining a healthy skin microbiota.

12 Claims, 3 Drawing Sheets

(56) References Cited

OTHER PUBLICATIONS

Daniel Bonner: "Introduction to Aerosols SATA Aerosol 101 CONTENT", Mar. 18, 2015 (Mar. 18, 2015), XP055435894.

* cited by examiner

Stability of the different formulations versus the pressurized canister 6 month at 20 °C

Fig. 5

AEROSOL SPRAY CONTAINING VIABLE BACTERIAL SPECIES

FIELD OF THE INVENTION

The present invention is directed to an aerosol spray containing one or more viable bacterial species and one or more volatile siloxanes suitable for applying said one or more viable bacterial species to a surface or into the environment.

BACKGROUND TO THE INVENTION

Aerosol sprays are very useful in the application of different agents to a surface or in the environment, and it would be an interesting way of formulating live bacterial species. However, in general, aerosol sprays comprise a watery component, which is incompatible with the formulation of live bacterial species. In particular, the presence of water normally also requires the presence of a preservative to prevent the growth of harmful pathogens and to control microbiological growth. Preservatives are harmful for the survival of co-formulated microorganisms. Furthermore, even Limited amounts of co-formulated water are sufficient to activate dormant bacteria, hereby significantly reducing the storage time for such compositions. Therefore, typical aerosol sprays are not suitable for the formulation of live bacterial species, and it was an object of the present invention to provide an aerosol composition which solves these problems of formulating and acquiring a long-term storage of live bacterial species.

Thereto, it was surprisingly found that aerosol sprays comprising at least one volatile siloxane is highly useful for said purpose.

Silicone fluids and siloxanes in particular, are often used in sprays comprising crop protection products, repellants, toiletry cosmetics and other personal care products. Most frequently used silicone fluids are the dimethicones, the cyclomethicones and phenyltrimethicones.

Incorporated into a product, these silicone fluids are highly suitable carrier oils with a large variety of benefits such as improved slip, reduction of tack and impartation of emolliency. Despite the low solubility and viscosity of cyclomethicones, these silicone fluids have been considered to be particularly useful when they are formulated in aerosol sprays, as they tend to provide the aforementioned benefits without contributing to oiliness or greasiness. Furthermore, it is known that cyclomethicone has a relatively high volatility and does not excessively block the antiperspirant active ingredient in deodorants. Finally, cyclomethicones are excellent dispersing and spreading agents, are generally water white in color, low in odor, are volatile, and are resistant to chemical and oxidative degradation.

Regardless of their widespread use in aerosol sprays, these silicone fluids are generally considered to have antimicrobial effects against a large range of (aerobic) bacteria, and have thus not been further investigated for formulating bacteria. Despite thereof, we have now surprisingly found that silicone fluids and in particular volatile siloxanes such as cyclomethicones can be used for long-term storage of (dormant lactic acid) bacteria in aerosol sprays. Such dormant bacteria were found not to be affected by the volatile siloxanes and thus remain stable during storage. After being sprayed the dormant bacteria become active due to contact with water or vapour, and by that time, the co-formulated volatile siloxanes have evaporated and do no longer influence the survival of the activated bacteria.

SUMMARY OF THE INVENTION

In a first aspect, the present invention provides an aerosol spray comprising 1-20 wt % of one or more viable probiotic bacterial strains, one or more volatile siloxanes and a propellant under pressure.

In a particular embodiment, said one or more viable bacterial species, more specifically viable probiotic strains, are dormant bacterial species more in particular dormant lactic acid bacteria.

In a specific embodiment of the present invention, said one or more siloxanes are selected from the list comprising linear siloxanes such as dimethicones, dimethiconols, phenyltrimethicones and derivatives thereof; or cyclic siloxanes, such as cyclomethicones and derivatives thereof; more in particular cyclic siloxanes, such as cyclomethicones and derivatives thereof.

In another particular embodiment, the present invention provides an aerosol spray comprising a mixture of one or more viable (preferably dormant) bacterial species and one or more volatile siloxanes, wherein said mixture is in the form of a powder, suspension or emulsion; wherein the aerosol spray of the present invention may further comprise a propellant.

Said propellant (under pressure) is in particular selected from the list comprising a liquefied gas more in particular one or more hydrocarbons such as methane, ethane, propane, isopropane, butane, n-butane, pentane and n-pentane; alternatively, the propellant may be a permanent compressed and/or soluble gas such as Nitrogen, Carbondioxide, Compressed air or nitrous Oxide gas.

In yet a further embodiment, the aerosol spray of the present invention may further comprise an anti-sedimentation and/or anti-agglomeration agent. Said anti-sedimentation and/or anti-agglomeration agents are in particular selected from a list of inorganic polymers such as organo-clay gels containing bentonite or hectorite; and/or fumed silica's such as aerosil.

In another particular embodiment, the aerosol spray of the present invention may further comprises one or more emollients, suspending agents, moisturizers, antioxidants, humectants, emulsifiers, viscosity modifying agents, perfumes and/or other excipients.

In a specific embodiment, the present invention provides an aerosol spray; wherein the content thereof comprises or consists of at least 50% propellant, 1-20% siloxanes, 1-20% lactic acid bacteria and 0.1-10% anti-sedimentation and/or anti-agglomeration agents.

In yet a further embodiment, the present invention provides an aerosol spray wherein the content thereof comprises or consists of at least 75% propellant, 5-10% cyclomethicone, 1-10% lactic acid bacteria and 0.1-5% bentone gel. Alternatively, the present invention provides an aerosol spray comprising or consisting of at least 75% propellant, 5-10% cyclomethicone, 1-10% lactic acid bacteria and 0.1-5% aerosil.

In a specific embodiment, the aerosol spray according to the present invention is substantially free of water and preservatives.

In a further aspect, the present invention provides the use of an aerosol spray according to the present invention for applying said one or more viable bacterial species; specifically said viable probiotic bacterial strains to a surface or into the environment.

In a specific embodiment the present invention provides an aerosol spray as defined herein for use in restoring and/or maintaining a healthy skin microbiota. The present invention thus also provides the use of an aerosol spray according to current invention for restoring and/or maintaining a healthy skin microbiota.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

FIG. 5: Stability of freeze dried LAC_15 In different silicones and silicone mixtures after 3 months. Although small differences were noted, most were deemed insignificant. There do seems to be a trend where a mixture of different silicon oils provides for a better stability than one or two oil components. This might indicate that a lower concentration of different silicon oils cancels out the negative influence of higher single concentration silicon components.

DETAILED DESCRIPTION OF THE INVENTION

In a first aspect, the present invention provides an aerosol spray comprising 1-20 wt % of one or more viable probiotic bacterial strains, one or more volatile siloxanes and a propellant under pressure.

More generally, the present invention provides an aerosol spray comprising a mixture of one or more viable (preferably dormant) bacterial species and one or more volatile siloxanes, wherein said mixture is in the form of a powder, suspension or emulsion. In a particular embodiment, said one or more viable bacterial species are dormant bacterial species; more in particular dormant lactic acid bacteria.

In the context of the present invention the term "aerosol spray" is meant to be a type of dispensing system which creates an aerosol mist. This is used with a can or bottle that contains the mixture of the present invention and preferably a propellant under pressure. When the container's valve is opened, the mixture is forced out of the canister through the valves and emerges as an aerosol or mist. As small amount of propellant expands to drive out the mixture, a large amount of propellant remains inside the can to maintain a constant pressure. Outside the can, the propellant evaporates rapidly.

In the context of the present invention, the term "mixture" is a system made up of two or more different substances which are mixed but are not combined chemically, such as a combination of volatile siloxanes and dormant bacterial species. In such mixture, the individual identities of the components are retained and they are mixed in the form of solutions, suspensions, emulsions, colloids or powders.

In the context of the present invention, the term "powder" is a dry, bulk solid composed of a large number of very fine particles that may flow freely when shaken or tilted. Powders are a special sub-class of granular materials, although the terms powder and granular are sometimes used to distinguish separate classes of material.

In the context of the present invention, the term "dormant" is meant to be a state of living/viable bacteria in which growth, development, reproduction, have temporarily stopped. They are in a metabolically dormant state in which metabolic processes are slowed down to such extent that they no longer produce significant amounts of metabolites. Many bacterial species can survive adverse conditions such as low temperature by forming (endo)spores, cysts, conidia or states of reduced metabolic activity lacking specialized cellular structures. Upon experiencing 'normal' conditions, dormant bacteria can be reactivated, such as after they come into contact with water or encountering a certain temperature or vibrations. In the context of the present invention, the bacteria may be brought in a dormant state using art known techniques such as freeze-drying, spray-drying, vacuum drying, fluid bed drying, nitrogen cryo drying . . . . Preferably, the bacteria of the present invention are freeze-dried.

In the context of the present invention the term "volatile" is used in relation to the disclosed siloxanes, to indicate that they have the tendency to vaporize. Volatility is directly related to a substance's vapor pressure. At a given temperature, a substance with higher vapor pressure vaporizes more readily than a substance with a lower vapor pressure. Otherwise, Substances with a lower heat of vaporization (kJ/kg) will evaporate more quickly at a given temperature than those with a higher heat of vaporization. The term is primarily written to be applied to liquids; however, it may be used to describe the process of sublimation which is associated with solid substances, such as dry ice (solid carbon dioxide), which can change directly from the solid state to a vapor, without becoming liquid. The vapor pressure of a substance is the pressure at which its gas phase is in equilibrium with its condensed phases (liquid or solid). It is a measure of the tendency of molecules and atoms to escape from a liquid or a solid. The higher the vapor pressure of a liquid at a given temperature, the higher the volatility and the lower the normal boiling point of the liquid. Preferably, the vapor pressure of the volatile siloxanes of the present invention is less than 2500 kJ/kg at room temperature (25° C.), more preferably less than 1000 and even more preferably, less than 900, 800, 700, 600, 500, 400, 300, 200 kJ/kg.

Cyclomethicones are a group of methyl siloxanes, a class of liquid silicones (cyclic polydimethylsiloxane polymers) that possess the characteristics of low viscosity and high volatility as well as being skin emollients and in certain circumstances useful cleaning solvents. Unlike dimethicones, which are linear siloxanes that do not rapidly evaporate, cyclomethicones are cyclic: both groups consist of a polymer featuring a monomer backbone of one silicon and two oxygen atoms bonded together, but instead of having a very long "linear" backbone surrounded by a series of methyl groups (which produces a clear, non-reactive, non-volatile liquid ranging from water-thin to taffy-thick), cyclomethicones have short backbones that make closed or nearly-closed rings or "cycles" with their methyl groups, giving them many of the same properties of dimethicones but making them much more volatile. Therefore dependent on the desired degree of evaporation, one may select a more volatile siloxane such as cyclomethicone, or instead a siloxane being less volatile such as dimethicone. Preferred, however are the more volatile siloxanes such a cyclomethicone and derivatives thereof.

Silicones are commonly used in the personal care industry (and many others) and are perceived, upon skin contact, as being smooth, velvety, nongreasy and nontacky (Handbook of Cosmetic Science and Technology Fourth Edition 2014; New York CRC Press; 204 AD. Pg. 321-329). They have a low surface energy, are moisture- and temperature-resistant, biocompatible, volatile and permeable, non-toxic and non-irritating. Silicones are polymers derived from silicon (Si), carbon, oxygen and hydrogen and can be linear, cyclic or organo-functional. The most common silicone (dimethicone) has an inorganic Si-oxide backbone with organic (2x methyl) pending groups on the SI. A silicon polymer has a range of 2 to a few thousand monomers and has viscosity's that can range from 0.65 cSt (hexamethyldisiloxane) to +1 million cSt cps. High viscosity fluids can form a protective film whilst low viscosity fluids are able to be emulsified and have better solubility with other ingredients. The organic groups can be modified to provide surface active properties. SI-o bonds are very free to move (Si-o is 0.2 kcal/mol; c-c is 3.3 kcal/mol rotation energy), have a strong bonding energy (si-o is 117 kcal/mol; c-c is 85 kcal/mol bonding strength) and are flat and long (Si-o angle is 130° C., length is 0.163 nm; c-c bond has a 112° angle and a length of 0.154 nm). This all makes for a very flexible and strong backbone. Polydimethylsiloxane (PDMS) also has a very low surface tension of 20 mM/m compared to ethanol (50 mM/m) and water (72 mM/m).[2] This causes for a complete surface coverage and excellent spreading agent, both being useful properties in the formulation of an aerosol. The lower molecular weight silicones have a high volatility, leaving no residue and providing a light skin feel. Due to their low heat evaporation (per gram) they do not need much heat from the skin to evaporate and consequently do not feel cold as compared to water or ethanol based products (See table 1).

TABLE 1

Heat of Vaporization for Some Volatile Fluids Used in Cosmetics.

| Fluid | Heat of vaporization - kJ/kg |
| --- | --- |
| PDMS, cyclic (DP = 4) | 172 |
| PDMS, cyclic (DP = 5) | 157 |
| Hexamethyldisiloxane | 192 |
| Ethanol | 840 |
| Water | 2257 |

PDMS polymers show a high permeability for gasses, which is linked to the solubility and diffusion coefficient (See table 2).

TABLE 2

Permeability Data for Some Volatile Fluids Used in Cosmetics

| Fluid | Water vapor permeability - g/m2/h |
| --- | --- |
| PDMS, cyclic (DP = 5) | 155.7 |
| PDMS, linear (12,500 cSt) | 107.4 |
| Silicone gum | 148.6 |
| Silicone resin | 110.5 |
| Mineral oil | 98.0 |
| Alkylmethylsiloxane (C30+) | 1.4 |
| Petrolatum | 1.3 |

This high gas diffusion rate causes for the skin to be able to "breathe" and is described as being non-occlusive. Cyclic silicones (cyclomethicone, D4-D5-D6) are very good solvents, non-staining, colorless, odorless and have a high volatility. They are most commonly used in antiperspirant products as delivery vehicle for active ingredients. They do not feel cold on the skin due to their low heat vaporization and have a pleasant skin feel and are the suspending medium of choice for pressurized aerosol canisters. They can also prevent the formation of agglomerates at the valves because of the lubricant properties of silicones. Other suspending mediums commonly used in antiperspirants are ethanol, water and mineral oils.

In the context of the present invention the term "siloxanes" is meant to be molecules comprising functional groups with the Si—O—Si linkage. The parent siloxanes include the oligomeric and polymeric hybrids with the formulae $H(OSiH_2)_nOH$ and $(OSiH_2)_n$. Siloxanes also include branched compounds, the defining feature of which is that each pair of silicon centres is separated by one oxygen atom. The siloxane functional group forms the backbone of silicones. Suitable volatile siloxanes within the context of the present invention may be selected from the list comprising linear siloxanes such as dimethicones, dimethiconols, phenyltrimethicones and derivatives thereof; or cyclic siloxanes, such as cyclomethicones and derivatives thereof; more in particular cyclic siloxanes, such as cyclomethicones and derivatives thereof.

It was found by the inventors that by pressurizing the aerosol cans, an even improved stability over non-pressurized compositions was achieved. Therefore, in another particular embodiment, the aerosol spray of the present invention may further comprise a propellant.

In the context of the present invention, the term "propellant" is meant to be a pressurized gas that is used to create movement of a fluid or powder. In particular, they are simply liquids (or gasses) that can readily be vaporized. Cold gas propellants may be used to fill in pressurised dispensing systems, such as aerosol sprays, to force a material through a nozzle. In aerosol spray cans, the propellant is usually a pressurized gas in equilibrium with its liquid or powder (at its saturated vapour pressure). As some gas escapes to expel the payload, more liquid evaporates, maintaining an even pressure. Suitable propellant useful within the context of the present invention may be selected from the list comprising a liquefied gas more in particular one or more hydrocarbons such as methane, ethane, propane, isopropane, butane, n-butane, pentane and n-pentane; or a permanent compressed and/or soluble gas such as Nitrogen, Carbondioxide, Compressed air or nitrous Oxide gas. Other liquefied gasses which may be used in the context of the present invention are DME (dimethylether) and HFC (hydrfluorcarbons) such as 1,1,1,2-tetrafluorethane and 1,1-difluorethaan.

In yet a further embodiment, the aerosol spray of the present invention may further comprise an anti-sedimentation and/or anti-agglomeration agent.

In the context of the present invention the term "anti-sedimentation agent" is meant to be substances which prevents particles in suspension from settling out of the fluid in which they are entrained and come to rest against a barrier, such as the bottom of the aerosol can. A good anti-sedimentation agent will have the properties of forming a porous, voluminous and easy resuspendable suspension, necessary for a homogeneous dosage. In the context of the present invention the term "anti-agglomeration agent" is meant to be substances that prevent caking or agglomeration of the components. Suitable anti-sedimentation and/or anti-agglomeration agents within the context of the present invention may be selected from the list comprising inorganic polymers such as organoclay gels containing bentonite or hectorite; and/or fumed silica's such as Aerosil®. The Aerosils® can be chemically modified to obtain a better 3D structural network in the selected siloxane carrier. Aerosils are typically hydrophilic fumed silica's ($SiO_2$). More particularly suitable for this invention are hydrophobic silica's, usually silicas aftertreated with hydrophobic substances such as, but not limited to: Dimethyldichlorislane, polydimethyliloxane, organosilane, hexadecylsilane, octamethylcyclotetrasiloxane, methacrylsilane, silicone oil, aminosilane and derivates thereof.

In another particular embodiment, the aerosol spray of the present invention may contain any further substances which may be useful in the context of the present invention. Such further substances include but are not limited to one or more emollients, moisturizers, antioxidants, humectants, suspending agents, emulsifiers, viscosity modifying agents, polarity modifying agents, perfumes, electrolytes, color modifying agents and other excipients. Suitable antioxidants might be, but are not limited to: BHT, BHA, propyl gallate, ascorbic acid & Sodium-metabisulfiet. Suitable viscosity modifying agents might be, but are not limited to, different colloids, silicone resins, propyleneglycol, organogels, aerosils, . . . .

A suitable additional component in the aerosol sprays of the present invention is for example Tegosoft®, i.e. polypropylene glycol butyl ether or ppg-14-butylether. Tegosoft® is a light cosmetic oil with very good spreading properties which is often used as an emollient in skin care products such as creams, lotions, bath oils, . . . . It also has excellent suspending properties for active ingredients in aerosol formulations. PPG-Butyl Ether ingredients in cosmetic formulations enhance the appearance of dry or damaged skin by reducing flaking and restoring suppleness.

Whenever in the context of the present invention percentages are mentioned, these are meant to be wt/wt percentage over the total compositions. For example 80% propellant is meant to be that 80 g of propellant is present in a total weight of the composition of 100 g.

In a specific embodiment, the present invention provides an aerosol spray of which the content comprises or consists of at least 10% propellant, 10-40% siloxanes, 10-40% lactic acid bacteria, 0-5% anti-sedimentation and/or anti-agglomeration agents and 0-5% of other additives.

In a specific embodiment, the present invention provides an aerosol spray of which the content comprises or consists at least 50% propellant, 1-20% siloxanes, 1-20% lactic acid bacteria, 0.1-5% anti-sedimentation and/or anti-agglomeration agents and 0-5% of other additives.

Preferably, the aerosol sprays of the present invention contain from 1-20% of lactic acid bacteria; more in particular from 1-10%; even more in particular about 9%, 8%, 7%, 6%, 5%, 4%, 3%, 2% or 1% of lactic acid bacteria.

Furthermore, the aerosol sprays of the present invention preferably contain a low amount of anti-sedimentation agents such as less than 5%, less than 4%, less than 3%, less than 2%, less than 1% or even no anti-sedimentation and/or anti-agglomeration agent if feasible.

In a specific embodiment, the present invention provides an aerosol spray of which the content comprises or consists of at least 75% propellant, 5-10% siloxanes, 1-10% lactic acid bacteria and 0-5% anti-sedimentation and/or anti-agglomeration agents.

In another specific embodiment, the present invention provides an aerosol spray of which the content comprises or consists of at least 80% propellant, 1-8% siloxanes, 1-8% lactic acid bacteria and 0-4% anti-sedimentation and/or anti-agglomeration agents.

In another specific embodiment, the present invention provides an aerosol spray of which the content comprises or consists of at least 90% propellant, 1-4% siloxanes, 1-4% lactic acid bacteria and 0-2% anti-sedimentation and/or anti-agglomeration agents.

In a specific embodiment of the compositions defined herein above, the anti-sedimentation and/or anti-agglomeration agent is selected from bentone gel and Aerosil®.

In yet a further embodiment, the present invention provides an aerosol spray of which the content comprises or consists of at least 75% propellant, 5-10% cyclomethicone, 1-10% lactic acid bacteria and 0-5% bentone gel. Alternatively, the present invention provides an aerosol spray of which the content comprises or consists of at least 75% propellant, 5-10% cyclomethicone, 1-10% lactic acid bacteria and 0-5% aerosil.

Evidently, in the formulation of dormant bacteria, harmful products such as preservatives and activating substances such as water are preferably avoided in order to ensure long-term storage of the composition. Therefore, in a specific embodiment, the aerosol spray according to the present invention is substantially free of water and preservatives. The term "substantially free" is meant to be less than 10%, 9%, 8%, 7%, 6%, 5%, 4%, 3%, 2%, preferably less than 1%. Wherein a multi-compartment aerosol spray is used, the compartment containing the bacteria is preferably substantially free of water and preservatives.

In a further aspect, the present invention provides the use of an aerosol spray according to the present invention for applying said one or more live bacterial species to a surface or into the environment. In the context of the present invention the term "surface" should be interpreted in its broadest sense, i.e. it may include surfaces of an object, however, it may also include the skin of humans or animals. Therefore the aerosol sprays of the present invention may also be topical aerosol sprays, wherein the term "topical" is meant to be the local delivery at a specified location of the body, in particular the application to a particular place on or in the body. In particular, it includes the application to mucous membranes via aerosols.

In a specific embodiment the present invention provides an aerosol spray as defined herein for use in restoring and/or maintaining a healthy skin microbiota. The present invention thus also provides the use of an aerosol spray according to the current invention for restoring and/or maintaining a healthy skin microbiota.

EXAMPLES

Introduction to the Examples

Athlete's foot and other dermal mycotic infections are currently treated with antimycotics such as miconazole that interferes with the ergosterol synthesis. A well-known commercial product containing miconazole is Daktarin® spray, preferred for its ease of use. Both antibiotics & antimycotics know an increasing trend in resistance. Therefore, alternative treatments such as the use of probiotics for topical diseases, would be beneficial for patients. Most probiotics exert beneficial effects for the host (human) by preventing the invasion & colonization of pathogens. Some probiotics, like *Lactobacillus* species, are able to combat those pathogens by excreting organic acids, hydrogen peroxide & antimicrobiological peptides into the environment. Common skin fungus infections such as tinea pedis are caused by different species such as *Trichophyton, Epidermophyton, Microsporum* and *Candida*. This study investigates whether an aerosol (pressurized canister) is a suitable formulation for the preservation and long term stability of probiotics.

As already proven, probiotics have a much better long-term stability when correctly dried as opposed to non-dried bacteria (Morgan et al., 2006—Preservation of micro-organisms by drying; a review—Journal of microbiological Methods 66 (2006) 183-193). The drying process brings the probiotics in a metabolically inactive state (i.e. dormant). The remaining water activity (Aw) of the powder, as well as the storage conditions (temperature, oxygen, light) will mainly determine the stability of the powder.

Example 1: Stability of Probiotic Bacteria in Silicones

In this example, we have examined the long term stability of viable probiotic bacteria in different silicone/siloxane mixtures Material and Methods
Stability Study
Three strains were used in this stability study:
Self-cultured *L. pentosus* (i.e. lac4 or Lp)
Self-cultured LGG (i.e. lac7 or LGG)
Purchased Freeze-dried LGG (Dupont® LR-32)
Two different silicone-based suspension media for preserving the bacteria were tested at room temperature (+/−20° C.):
Silicones:
Cosmetic fluid 1406-OH (dimethiconol & dimethicone)—Chemsil®
Cosmetic fluid 6570-DM (disiloxane, cyclopentasiloxane & dimethicone)—Chemsil®

Samples were obtained at pre-defined timepoints:
T0=before suspension in the suspension media
T1=1 day after suspension
T2=1 week after suspension
T3=2 weeks after suspension
T4=1 months after suspension
T5=2 months after suspension
T6=6 months after suspension
T7=12 months after suspension All used materials were sterilized before use by autoclaving. All used components, ingredients, . . . were autoclaved if possible, and otherwise filtered in sterile circumstances before suspending the bacteria.

T0 CFU Determination

Lac 4 & Lac 7 were cultured in liquid MRS (de MAN, Rogosa & Sharpe-Carl Roth) medium (37° C.) until fully grown. The medium was centrifuged for 10 minutes at 2780 G. The supernatant was disposed and the bacterial pellet was further used.

100 mg was weighed and diluted with physiological water (0.85% NaCl) to obtain a total volume of 10 ml. From the three strains (lac 4, lac 7 and LGG), dilution series were made (10-fold serial dilutions) and plate counting happened according to the spread plating method (Derived from Pharmacopeia methods 2.6.12 and 2.6.13. (European Pharmacopeia 8.0). Measurements were repeated in triplicate. Results are expressed as cfu/gram powder.

Suspension of the Bacteria in the Suspension Media

With the obtained bacterial masses, a homogenous $^1/_{10}$ dilution (m/m %) was made with the different anhydrous silicone-based suspension media. 1 gram of said suspension was weighed in a falcon tube and sealed in an aluminum bag (RH=20%). Each sample hereby contained 100 mg bacteria for further testing purposes. Aluminum bags were opened at certain time intervals for viability testing.

Testing after Storage Time

The sealed bags were opened at certain time points for stability testing. The falcon tube containing 1 gram of anhydrous substance was further processed by adding 1 gram of an emulsifier mixture (consisting of polysorbate 80 & sorbitansesquioleate) and 8 gram of physiological water. This formed an emulsion through which the bacteria could get into contact with water and were reactivated. Further sample preparation and plate counting happened as described above and was derived from pharmacopeia (8.0) method 2.6.12: Microbiological examination of non-sterile products: microbial enumeration tests and 2.6.13: microbiological examination of non-sterile products: test for specified micro-organisms.

Results and Discussion

Figure 1:
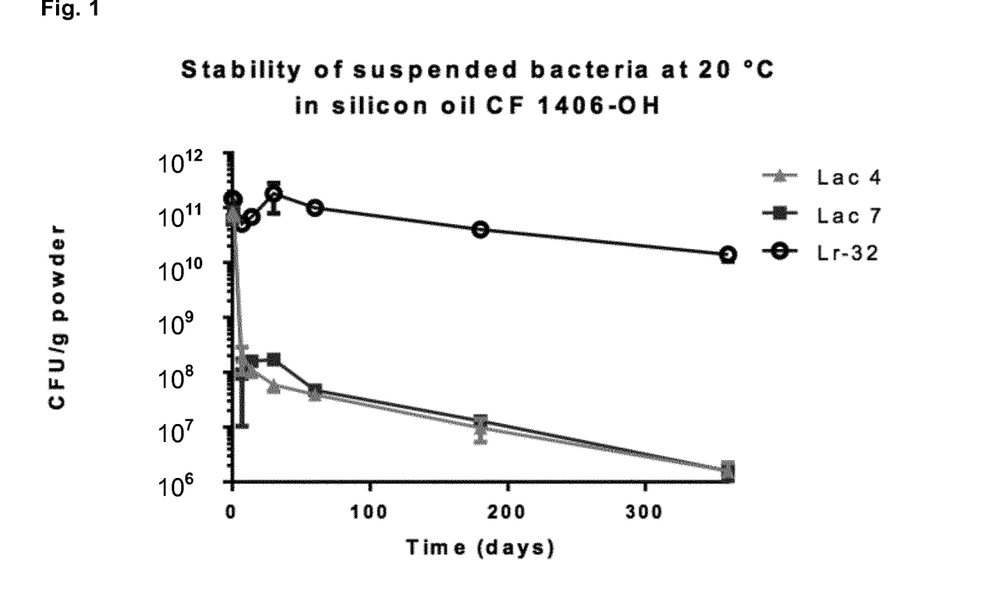
FIG. 1: Stability of self-cultured (non-dried) Lac 4 & Lac 7 vs a commercial freeze dried strain of LGG, suspended (1/10 m/m %) in silicon oil CF 1406-OH over a period of 1 year. This figure clearly shows that freeze drying probiotics and suspending them in an anhydrous silicon mixture is an ideal way for preventing a fast drop in viability of the viably bacteria. Suspending the freeze dried bacteria in a silicon mixture containing dimethicone and dimethiconol provides for a long term storage of this *Lactobacillus* species.
Figure 2:
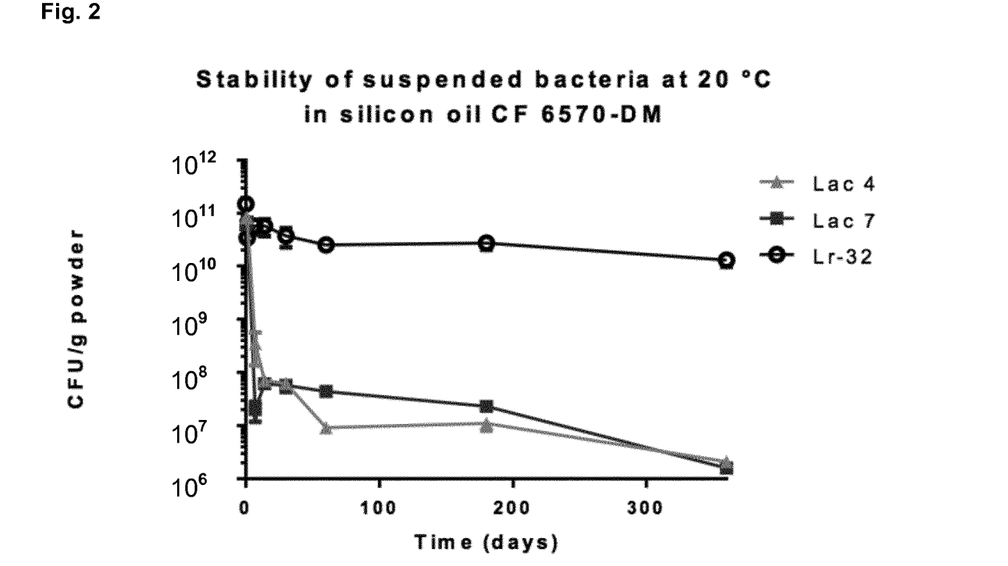
FIG. 2: Stability of self-cultured (non-dried) Lac 4 & Lac 7 vs a commercial freeze dried strain of LGG, suspended (1/10 m/m %) in silicon oil CF 6570-DM over a period of 1 year. This figure clearly shows that freeze drying probiotics and suspending them in an anhydrous silicon mixture is an ideal way for preventing a fast drop in viability of the viably bacteria. Suspending the freeze dried bacteria in a silicon mixture containing dimethicone, disiloxane and cyclopentasiloxane provides for a long term storage of this *Lactobacillus* species.

The stability of the freeze dried powder was far more superior, as expected, compared to that of the non freeze dried strains. After just 1 month, and regardless of the type of silicon mixture used (FIG. 1: CF1406; FIG. 2: CF6570) there is on average a 3 log reduction whilst there is no significant reduction detectable for the freeze dried strain (FIGS. 1 & 2). Hereby it is proven that it is important to start formulating with a properly freeze dried (or other drying method) powder to ensure a stable formulation of viable micro-organisms over time. A stable dried probiotic powder is easier to handle for further formulating purposes.

The stability results for the silicon mixtures (FIGS. 1 & 2), indicate that these are suitable as a suspending medium. While there is an average of 1 log reduction after 1 year stability for the anhydrous silicone media, this leaves enough viable micro-organism to be applied topically and exert a beneficial effect on the skin.

Hereby it is proven that working with a properly freeze dried powder, suspended in an anhydrous silicone medium, it is possible to obtain a suspension with stable probiotics.

Example 2: Stability of Probiotic Bacteria in Pressurized Aerosol Formulation In this example, we have examined the long term stability of viable probiotic bacteria formulated in a pressurized aerosol composition.
Material and Methods A freeze dried strain of *L. plantarum* (THT®-Freeze dried with maltodextrine) was sieved to obtain a powder fraction with a particle size <50 micron, to ease passing of the valve and nozzle and to prevent blockage. The bacteria were suspended in Mirasil CM5® (decamethylcyclopentasiloxane), a volatile cyclomethicone and/or Tegosoft PBE® (propoxylated alcohol-ppg 14 butylether), both acting as suspending media. An organoclay component, bentone gel vs5 PC V® (cyclopentasiloxane, disteardimonium hectorite & propylene carbonate), was used as anti-sedimentation and anti-agglomeration agent.

A total of 8 formulations (concentrates) were prepared in different concentrations (see table 3), before filling with propellant in the aerosol canisters.

TABLE 3

Compositions of the different formulations: The concentrate is filled in canisters (20%) after which 80% propellant is added, making a 5-fold dilution of the concentrate.

| Sample | Ingredients | % in concentrate | % in canister |
|---|---|---|---|
| 1 | L. Plantarum | 5 | 1 |
|   | Bentone gel | 5 | 1 |
|   | Mirasil | 90 | 18 |
|   | Tegosoft | 0 | 0 |
| 2 | L. Plantarum | 5 | 1 |
|   | Bentone gel | 25 | 5 |
|   | Mirasil | 70 | 14 |
|   | Tegosoft | 0 | 0 |
| 3 | L. Plantarum | 25 | 5 |
|   | Bentone gel | 5 | 1 |
|   | Mirasil | 70 | 14 |
|   | Tegosoft | 0 | 0 |
| 4 | L. Plantarum | 20 | 4 |
|   | Bentone gel | 20 | 4 |
|   | Mirasil | 60 | 12 |
|   | Tegosoft | 0 | 0 |
| 5 | L. Plantarum | 5 | 1 |
|   | Bentone gel | 0 | 0 |
|   | Mirasil | 95 | 19 |
|   | Tegosoft | 0 | 0 |
| 6* | L. Plantarum | 5 | 1 |
|   | Bentone gel | 5 | 1 |
|   | Mirasil | 90 | 18 |
|   | Tegosoft | 0 | 0 |
| 7 | L. Plantarum | 5 | 1 |
|   | Bentone gel | 0 | 0 |
|   | Mirasil | 47.5 | 9.5 |
|   | Tegosoft | 47.5 | 9.5 |
| 8 | L. Plantarum | 5 | 1 |
|   | Bentone gel | 0 | 0 |
|   | Mirasil | 0 | 0 |
|   | Tegosoft | 95 | 19 |

*A sieve fraction <30 micron was used for sample 6, as opposed to all the other formulation samples that have a powder fraction <50 micron.

The canisters were evaluated for viability of the bacteria as well as for the spray characteristics and residue & sedimentation properties of the suspended powder. Too much sedimentation can result in caking and consequently failure of product release or may lead to frequent nozzle blockages. The canisters are filled with 20% formulation and 80% propellant. The propellant used is a mixture of LPG (Propane/Butane/Isobutane—29/69/2) & Butane (55/45). Under pressure (±2-4 bar), it is present as a liquefied propellant.

Reference fractions (1 gram) of the different formulations were kept in sealed aluminum bags at room temperature (T=20° C.) for CFU determination. The CFU's acquired from the aerosol canisters, also stored at room temperature (20° C.), were compared with the references to evaluate the effect of filling and storage. A bacterial load determination of the powder was done right before formulation preparation and filling of the canisters, which resulted in 5, 9.0E+11 CFU/g bacterial powder as starting concentration. Further sampling happened after 1, 2, 3, 4, 6 & 12 months of storage. Results were calculated as CFU/g bacterial powder.

CFU determination of the formulations was performed by adding 1 gram of emulsifier mixture (70% tween 80/30% span 83) and 8 gram of physiological water, shaken until dissolved, followed by a 10-fold serial dilution. Plating was performed according to the "Copacabana method" (Spread plating with glass beads) followed by CFU counting after 3 days of incubation at 37° C. All materials and liquids used were sterilized through autoclaving.

CFU determination of the aerosol canisters was performed by spraying 5 grams from the canister and waiting (±1 hour) until all the propellant had evaporated. Consequently 1 gram of formulation remained in the recipient. Further sample preparation was performed as described above.

All samples were tested in 3 biological repeats (3 samples) and 3 technical repeat (plate counts) values before an average and deviation was calculated with the following formula:

$$\frac{CFU}{g}\text{powder} = \left(\frac{CFU \times \text{Dilution factor}}{g\,(ml)\text{on plate}}\right) \times \left(\frac{g\,\text{powder in sample} + g\,\text{dilution medium}}{g\,\text{powder}}\right)$$

Figure 3:
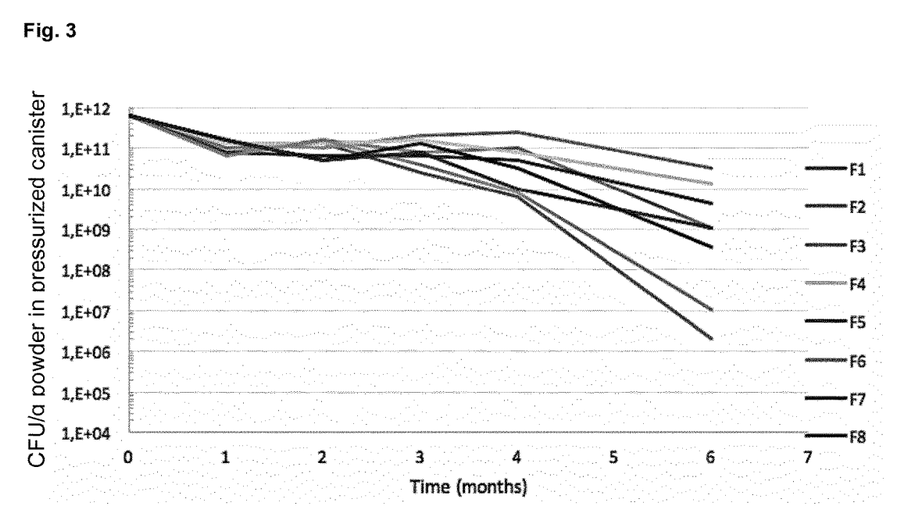
FIG. 3: Survival curves of suspended freeze-dried *L. plantarum* in different formulations (F1-F8), whilst being stored in a pressurized canister with hydrocarbon propellants at room temperature (20° C.). After a small initial drop in viability during the first month, the viability remains rather constant during the following months proving that storage in a pressurized canister is a suitable method for long term survival of probiotics.

An extra set of canisters of each formulation was kept unopened at 20° C., emptied (after shaking) after 6 months and were evaluated for their spray characteristics and residue in the canister after emptying.
Results and Discussion The survival curves of *L. plantarum* in the filled canisters show an average 1-log decrease after 1 month of storage stability (FIG. 3). This indicates a small drop in viability right after or during the filling of the canisters. There are some possible explanations for this phenomenon. The propellant gas is kept under its partial pressure (±4 bar) before filling. Under a slight overpressure, the liquid is filled in the canister where it mixes with the present formulation, thus the present bacteria experience a pressure shock. Another explanation might be that during the use of the canister, by opening the valve nozzle, aerosol formation is paired with high shear forces to eject the bacterial powder from the canister. A last explanation might be that the endothermic reaction paired with the evaporation of the propellant causes for a sudden temperature drop of the remaining formulation. All three stresses (pressure shock, shear forces & temperature shock) are well described in the literature as being harmful for the bacteria, influencing the viability.

On the other hand, in the time-frame between 1 month and 4 months after filling, the viability in the filled canisters remains rather interestingly constant, with a maximal drop of 0.5-1 Log in viability. In the timeframe between 4 and 6 months of stability, the viability decreased with a couple of logs more for some formulations. The start-to-end (6 month) viability-drop was a 1-log reduction for F3, a 2-log reduction for F4 and F5, a 3-log reduction for F8, F1 and F7; and a 5-log reduction for the F6 and F2 canister. These data indicate that a stability of 4 months can be guaranteed for all pressurized formulations, and that depending on the desired time of stability, a suitable formulation can be selected to guarantee stability over a period of 6 months and longer. From these results (FIG. 4) it is clear that inclusion of the formulations in a hydrocarbon propellant pressurized canister has a positive effect on the viability of *L. plantarum* in the formulation. This indicates a stabilization of the formulation after the inevitable initial loss of viability during the first month of storage. The hypothesis is that the hydrocarbon propellant mixture, creates a water and oxygen-free environment, supporting the survival of freeze dried *Lactobacillus* species. Some studies in literature describe the improved survival for *Lactobacillus* bacteria when stored under inert gasses such as nitrogen and carbon dioxide or when stored under vacuum. However, no reports of survival under hydrocarbon gasses/liquids in siloxane based-media have been published yet.

The viability of *L. plantarum* after storage was the highest in Formulation 3 (25% probiotics), in addition, Formulation 4 (20% probiotics) also showed good viability. Apparently, the formulations with a high concentration of bacteria (F3, F4) have a good stability, even if corrected for initial loading percentages. This might be attributed to a mutual shielding effect against severe conditions of the external medium. When assessing the effect of bentone gel in the pressurized canisters (F5 vs F1 and F2—in increasing concentrations 0-5-25%), it showed a slight difference in log reduction between F5 (2.2 [1.9-2.9] LOG) and F1 (2.8 [2.6-3.1]log) and a bigger difference with F2 (5.5 [5.3-5.9]log). Hence, it can be concluded that the formulations preferably contain no or only a low amount of anti-sedimentation agents such as bentone gel.

The viability in F1 (50 m) is significantly (2-log) higher than F6 (30 m), indicating that a smaller particle size is worse for the survival. A smaller particle size effects in a bigger surface area, thus more negative influences from the environment (formulation) can harm the bacteria. Hence, the formulations of the present invention preferably have a particle size larger then 30 micron.

Addition of propoxylated ppg-14-butylether (an oil like, volatile skin care agent and emollient), such as Tegosoft® (F7 and F8) had no negative effect on the stability in the filled canisters (FIG. 3). Hence, it can be concluded that such components can be added without adverse effects, but for example for improving the aerosol formation and aiding in complete emptying of the aerosol.

FIG. 4 shows a comparison of the different formulations as such or under pressure in the filled canisters. These date clearly show that pressurizing the formulations significantly increases the viability of the bacteria for all formulations over a time of 6 months.

In this experiment it was proven that a formulation of freeze dried bacteria suspended in volatile silicones, kept under pressure using a carbon hydrogen propellant is a suitable delivery system for the long term preservation of probiotics at room temperature. After expulsion of the spray out of the canister, the volatile components (propellant and silicones) will evaporate, leaving the freeze dried bacteria onto the skin or surface it was sprayed on. At this site of administration, the formulation will come in contact with the skin and the environment. The hygroscopic probiotic powder will absorb water from the surroundings and the bacteria will become metabolically active, being able to exert their beneficial function.

Example 3: Stability of Probiotic Bacteria in Different Silicones and Silicone Mixtures The goal of this example was to obtain a screening platform wherein the influence of different silicones and silicone-mixtures was evaluated on the viability of freeze dried *L. plantarum*. Comparisons were made for cyclic vs linear silicone molecules. Also the chain length (# siloxane molecules—Viscosity) was taken into comparison as smaller molecules might penetrate the cell more, disturbing metabolic processes once active again. Finally, the hypothesis that a mixture of silicones might cancel out the negative effects of different individual silicones, unless the negative effects are cumulative, was evaluated. These extensive comparative stability studies allow us to formulate a more stable aerosol formulation containing freeze dried *Lactobacillus* species, suspended in silicon oils for topical use.

For this experiment, freeze dried *L. plantarum* powder was suspended 1/25 (m/m %) in different silicones or silicone mixtures (see table 4), commonly used in antiperspirants.

TABLE 4

Different silicone compositions wherein freeze dried *L. Plantarum* is suspended 1/25 (m/m %).

| Formula | Suspending medium ingredients |
|---|---|
| 1. | Dimethicone 1 cSt |
| 2. | Dimethicone 5 cSt |
| 3. | Mirasil ® cm-5 (decamethylcyclopentasiloxane) |
| 4. | Dow corning ® 345 (cyclopentasiloxane, cyclohexasiloxane 70/30 - 6 Cst) |
| 5. | Hexamethyldisiloxane (0.65 cSt) |
| 6. | CF 6570-DM (Disiloxane, Cyclopentasiloxane and dimethicone - 300 cSt) |
| 7. | Dimethicone 5 Cst - Mirasil ® Cm-5 (50/50) |
| 8. | Dimethicone 5 Cp - DC 345 (50/50) |
| 9. | Dimethicone 5 Cp - Hexamethyldisiloxane (50/50) |
| 10. | DC ® 345 - Hexamethyldisiloxane (50/50) |
| 11. | Dimethicone 5 cSt - DC 345 - PPG-14-butylether (40/40/20) |
| 12. | Dimethicone 5 cSt - DC 345 - Hexamethyldisiloxane (40/40/20) |
| 13. | Dimethicone 1 cSt - Dimethicone 5 cSt - Mirasil ® cm5 - DC ® 345 - Hexamethyldisiloxane, 14-ppg butylether (all at 16.7%) |

The higher viscosity silicone CF 6570 was used as reference silicone as this mixture was previously used in the stability study of example 1. Different fractions of 1 gram were weighed in falcon tubes and stored in laminated aluminum pouches (Daklapack®—PET/ALU/NY/LDPE) to protect from light, oxygen and relative humidity and stored at room temperature (20° C.). A T0 determination of the powder was performed before making the suspensions and resulted in (5.85±0.71) E+11 CFU/gram. Further sampling was performed after 1 week, 2 weeks, 1, 3 and 6 months. During sampling, 3 falcon tubes of the same sample were taken and plates were counted in triplicate as described in 2.1. Blanc samples (reference) were stored as 100 mg powder (not-suspended).

Results and Discussion

It is clear from FIG. 5 that for all formulations a high stability ($10^9$ log CFU/g) of the compositions was achieved over a 3 month storage time, with some scoring slightly better than others such as the reference powder, F11 and in lesser extent F10. The differences were too small too make solid conclusions on the effect cyclic vs linear silicones and the chain length of siloxanes; which may indicate that these aspects are not highly relevant for a siloxane to be useful in the present invention.

Figure 5:
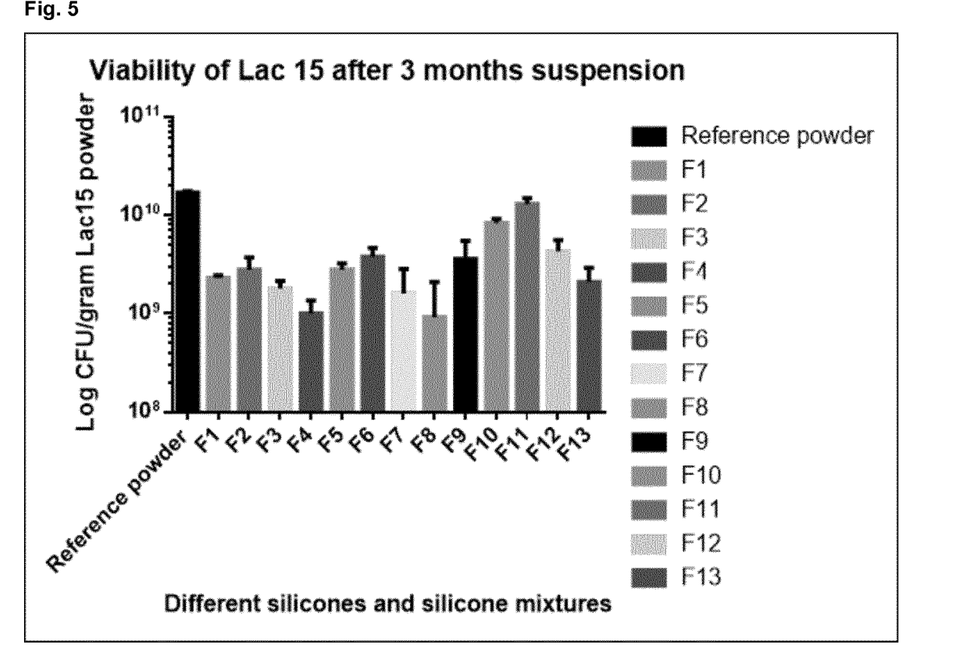

The single silicone components are shown on the left-hand side of FIG. 5 and the more complex mixtures (3-5 components) are on the right-hand side. In general, the silicone mixtures on the right-hand side of FIG. 5, show a better survival compared to the single silicones on the left, indicating that a mixture of different components (partially) cancels out some negative effect observed for the single component silicones.

Figure 4:
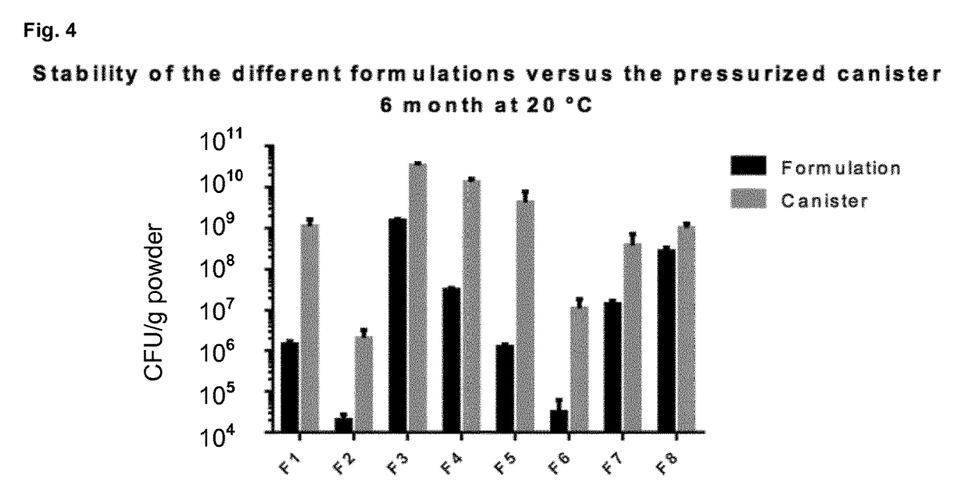
FIG. 4: Six month stability of freeze-dried *L. plantarum* in different formulations versus the same formulations stored in pressurized canisters. After 6 months of storage, there is a statistical significant difference in survival for the formulations stored with propellant in a pressurized canister, than the formulations stored without propellant. The survival was better for all 8 tested formulations, proving that suspending freeze dried bacteria in a silicon oil, stored with propellant is a better method for long term stability than simply suspending the freeze dried bacteria in a silicon oil.

Tegosoft® (ppg-14 butylether) is a biodegradable and moderately volatile propylene glycol n-butyl ether commonly found in antiperspirants. It has no negative influence on the stability of freeze dried bacteria in a pressurized aerosol canister compared to cyclopentasiloxane (FIG. 3-4). It seems that it even can have a protective effect on the survival of freeze dried bacteria once mixed with other silicones. (FIG. 5—F11 and F13). This in addition with its good suspending and spray characteristics and low residue in the canister indicates that the addition of polypropylene glycol ethers might be a valuable additional ingredient in formulating a probiotic aerosol.

The invention claimed is:

1. An aerosol spray consisting of:
   1-20 wt % of one or more viable, dormant, probiotic bacterial strains,
   1-20 wt % of one or more volatile siloxanes,
   0.1-5 wt % anti-sedimentation and/or anti-agglomeration agents,
   at least 50 wt % liquefied gas propellant under pressure, and
   0-5 wt % other excipients,
   wherein said one or more viable, dormant, probiotic bacterial strains and said volatile siloxanes form a mixture in the form of a suspension, and wherein the one or more volatile siloxanes in combination with the at least 50 wt % liquefied gas propellant under pressure maintain the viability of the one or more viable, dormant, probiotic bacterial strains for at least 6 months.

2. The aerosol spray according to claim 1, wherein the one or more volatile siloxanes are selected from the group consisting of linear siloxanes and cyclic siloxanes.

3. The aerosol spray according to claim 2, wherein:
   the linear siloxanes are selected from the group consisting of: dimethicones, dimethiconols, phenyltrimethicones, and derivatives thereof; and
   the cyclic siloxanes are selected from the group consisting of: cyclomethicones and derivatives thereof.

4. The aerosol spray according to claim 1, wherein the anti-sedimentation and/or anti-agglomeration agent is an inorganic polymer selected from the group consisting of: organoclay gels containing bentonite, organoclay gels containing hectorite, and fumed silicas.

5. The aerosol spray according to claim 4, consisting of:
   at least 75 wt % liquefied gas propellant under pressure,
   1-10 wt % viable, dormant, probiotic bacterial strains,
   5-10 wt % volatile siloxane, wherein the volatile siloxane is cyclomethicone, and
   0.1-5 wt % organoclay gel comprising bentonite, wherein the organoclay gel comprising bentonite is bentone gel.

6. The aerosol spray according to claim 4, consisting of:
   at least 75 wt % liquefied gas propellant under pressure,
   1-10 wt % viable, dormant, probiotic bacterial strains,
   5-10 wt % volatile siloxane, wherein the volatile siloxane is cyclomethicone, and
   0.1-5 wt % fumed silica.

7. The aerosol spray according to claim 1, wherein the other excipients are selected from the group consisting of: emollients, suspending agents, moisturizers, antioxidants, humectants, emulsifiers, viscosity modifying agents, or perfumes, and combinations thereof.

8. The aerosol spray according to claim 1, wherein the aerosol spray is free of water and preservatives.

9. The aerosol spray according to claim 1, wherein the one or more viable, dormant, probiotic bacterial strains are dormant lactic acid bacteria.

10. The aerosol spray according to claim 1, wherein the liquefied gas propellant is one or more hydrocarbons selected from the group consisting of: methane, ethane, propane, isopropane, butane, and pentane.

11. A method for restoring and/or maintaining a healthy skin microbiota, the method comprising topically applying the aerosol spray according to claim 1 to skin of a human or animal.

12. A method for cleaning a surface, the method comprising applying the aerosol spray according to claim 1 to the surface.

* * * * *

UNITED STATES PATENT AND TRADEMARK OFFICE
CERTIFICATE OF CORRECTION

| | | |
|---|---|---|
| PATENT NO. | : 11,980,646 B2 | Page 1 of 1 |
| APPLICATION NO. | : 16/344630 | |
| DATED | : May 14, 2024 | |
| INVENTOR(S) | : Tim Henkens et al. | |

It is certified that error appears in the above-identified patent and that said Letters Patent is hereby corrected as shown below:

In the Specification

In Column 3, Line(s) 65, after "There", delete "do".

In Column 4, Line(s) 58, delete "cryo drying....", insert --cryo drying,...--, therefore.

In Column 13, Line(s) 40, delete "(50 m)" and insert --(50 μm)--, therefor.

In Column 13, Line(s) 41, delete "(30 m)" and insert --(30 μm)--, therefor.

Signed and Sealed this
Seventeenth Day of September, 2024

Katherine Kelly Vidal
*Director of the United States Patent and Trademark Office*